United States Patent
Linne et al.

(10) Patent No.: US 9,522,366 B2
(45) Date of Patent: Dec. 20, 2016

(54) DYNAMIC MIXER

(75) Inventors: Volker Linne, Rosenthal-Roda (DE);
Andreas Hiemer, Rebstein (CH);
Florian Husler, Zug (CH)

(73) Assignee: SULZER MIXPAC AG, Haag (CH)

( * ) Notice: Subject to any disclaimer, the term of this patent is extended or adjusted under 35 U.S.C. 154(b) by 106 days.

(21) Appl. No.: 14/001,809

(22) PCT Filed: Jan. 27, 2012

(86) PCT No.: PCT/EP2012/051376
§ 371 (c)(1),
(2), (4) Date: Aug. 27, 2013

(87) PCT Pub. No.: WO2012/116863
PCT Pub. Date: Sep. 7, 2012

(65) Prior Publication Data
US 2013/0329517 A1    Dec. 12, 2013

(30) Foreign Application Priority Data
Feb. 28, 2011   (EP) .................................... 11156134

(51) Int. Cl.
*B01F 7/00* (2006.01)
*A61C 9/00* (2006.01)
(Continued)

(52) U.S. Cl.
CPC ......... *B01F 7/00008* (2013.01); *A61C 9/0026* (2013.01); *B01F 5/061* (2013.01);
(Continued)

(58) Field of Classification Search
CPC ........................ B01F 7/0025; B01F 7/00258
See application file for complete search history.

(56) References Cited

U.S. PATENT DOCUMENTS 3,293,117 A   12/1966 Pennington, Jr. et al.
5,249,862 A   10/1993 Herold et al.
(Continued)

FOREIGN PATENT DOCUMENTS

AU    2008297444 A1   3/2009
CN       1070843 A    4/1993
(Continued)

OTHER PUBLICATIONS

International Search Report for International Patent Application No. PCT/EP2012/051376 mailed on Apr. 19, 2012.
(Continued)

*Primary Examiner* — Tony G Soohoo
*Assistant Examiner* — Elizabeth Insler
(74) *Attorney, Agent, or Firm* — Global IP Counselors, LLP (57) ABSTRACT

A dynamic mixer (1, 100) for a plurality of fluid components contains a housing (2, 102) and a rotor element (3, 103) which is rotatably arranged in the housing, with the housing having an inlet opening (12, 13, 112, 113) for at least one respective component and having at least one outlet opening (20, 120). A ring-shaped intermediate space (15, 115) is provided between the rotor element and the housing in which a mixing element (7, 107) connected to the rotor element (3, 103) is arranged. The housing includes a first antechamber (21, 121) and a main chamber (22, 122). A second antechamber (17, 117) is provided which is arranged downstream of the first antechamber (21, 121) so that the first antechamber (21, 121) can be flowed through by the components before the components enter into the second antechamber (17, 117).

15 Claims, 8 Drawing Sheets

(51) Int. Cl.
- *B01F 5/06* (2006.01)
- *B01F 13/00* (2006.01)
- *B01F 13/10* (2006.01)
- *B05C 17/005* (2006.01)

(52) U.S. Cl.
CPC ...... *B01F 7/00125* (2013.01); *B01F 7/00133* (2013.01); *B01F 7/00141* (2013.01); *B01F 7/00216* (2013.01); *B01F 7/00258* (2013.01); *B01F 7/00291* (2013.01); *B01F 7/00641* (2013.01); *B01F 7/00775* (2013.01); *B01F 13/002* (2013.01); *B01F 13/103* (2013.01); *B01F 13/1027* (2013.01); *B05C 17/00566* (2013.01); *B01F 2005/0631* (2013.01); *B01F 2005/0636* (2013.01); *B01F 2215/0027* (2013.01); *B01F 2215/0039* (2013.01)

(56) References Cited

U.S. PATENT DOCUMENTS

| | | | |
|---|---|---|---|
| 5,863,120 | A | 1/1999 | Gallagher et al. |
| 6,193,408 | B1 | 2/2001 | Miura et al. |
| 6,394,643 | B1* | 5/2002 | Bublewitz ............ A61C 5/064 222/145.6 |
| 6,443,612 | B1 | 9/2002 | Keller |
| 6,523,992 | B1* | 2/2003 | Bublewitz ............ A61C 5/064 222/145.6 |
| 6,932,243 | B2* | 8/2005 | Keller ................ B01F 7/00141 222/145.6 |
| 7,230,037 | B2 | 6/2007 | Sulzbach et al. |
| 2004/0198870 | A1 | 10/2004 | Sulzbach et al. |
| 2004/0257909 | A1* | 12/2004 | Pieroni ................ A61C 5/064 366/172.1 |
| 2008/0056061 | A1* | 3/2008 | Pauser et al. ............ 366/152.2 |
| 2009/0034357 | A1* | 2/2009 | Gramann et al. ............ 366/77 |
| 2009/0207685 | A1 | 8/2009 | Busin et al. |
| 2009/0296516 | A1* | 12/2009 | Keller ................ A61C 5/064 366/160.5 |
| 2010/0208544 | A1* | 8/2010 | Wintergerste et al. ....... 366/134 |

FOREIGN PATENT DOCUMENTS

| | | |
|---|---|---|
| DE | 9017323 U1 | 4/1992 |
| DE | 102 42 100 A1 | 3/2004 |
| DE | 10 2007 059 078 A1 | 6/2009 |
| DE | 10 2008 008 964 A1 | 8/2009 |
| EP | 1 099 470 A1 | 5/2001 |
| EP | 1149627 A2 | 10/2001 |
| JP | 2000262882 A | 9/2000 |
| RU | 2264850 C2 | 11/2005 |
| TW | 358135 | 5/1999 |
| WO | 0021652 A1 | 4/2000 |
| WO | 2004-080611 A1 | 9/2004 |
| WO | 2007-041878 A1 | 4/2007 |
| WO | 2009071318 A2 | 6/2009 |

OTHER PUBLICATIONS

Written Opinion for International Patent Application No. PCT/EP2012/051376 mailed on Apr. 19, 2012.
International Search Report for International Patent Application No. 201280010729.6 dated Nov. 25, 2014.
Chinese Search Report for Chinese Patent Application No. 201280010729.6 dated Nov. 25, 2014.

\* cited by examiner

DYNAMIC MIXER

PRIORITY CLAIM

The present application is a National Stage of International Application No. PCT/EP2012/051376, filed on Jan. 27, 2012, which claims priority to European Patent Application No. 11156134.6 filed on Feb. 28, 2011, the entire contents of which are being incorporated herein by reference.

The invention relates to a dynamic mixer. A dynamic mixer of this type is advantageously used to mix a plurality of components which are supplied from a multicomponent cartridge.

A dynamic mixer is known from WO 2007/041878 for mixing components having different volume proportions, in particular for manufacturing dental impression materials. An antechamber is arranged in the inner space of the mixer housing within which the mixing rotor has a distribution body for distributing the components about its axis of rotation in order thereby to achieve a correct mixing ratio between the components and to avoid air inclusions. Subsequently, the premixed components move into a main chamber through at least one passage opening for their complete mixing.

It is particularly difficult to keep the correct mixing ratio constant and to maintain a good mixing in particular for high mixing ratios of viscous or pasty components. The mixing generally takes place by shear forces, with the components being urged through the mixer. The mixer has a housing and a rotor element which is rotatably arranged in the housing, the housing having one respective inlet opening for at least two components and at least one outlet opening. A ring-shaped intermediate space is provided between the rotor element and the housing in which there is arranged a mixing element attached to the rotor element.

The rotor element comprises the body element and the mixing element. This mixing element is formed as a vane element which projects away from the body element into the intermediate space. Preferably, a plurality of such vane elements are present. In addition, static mixing elements can also project from the inner wall of the housing into the intermediate space, which are, however, difficult to manufacture. The components are rearranged repeatedly by the vane element or elements and by the optionally provided static mixing elements in a kneading manner.

It is furthermore known from WO2007/041878 to divide the intermediate space into an antechamber and a main chamber. The antechamber serves the purpose of delaying the conveying of a component A in comparison with a component B so that the component A reaches the main chamber later than the component B. It is hereby ensured that the first portion of the mixture corresponds to the desired mixing ratio. A distributor body connected to the rotor element is used to ensure a filling of the antechamber with the component A and its distribution which is free of bubbles. As the distributor body is moved along with the rotor element, the liquid resistance and consequently the pressure loss remains low. It is furthermore ensured that the smallest possible distance is observed between the inlet opening and the lead chamber so that the liquid resistance can remain small. On the contrary, it is disadvantageous that the two components arrive at the main chamber substantially unmixed.

In order to achieve a mixing effect it is aimed to produce a phase boundary area between the components which is as large as possible to generate a plurality of fine layers by dividing and rearranging the flowing components. For this purpose, the components were commonly directed from the antechamber into the main chamber in which the components were contacted for the first time. In the main chamber, the fluid mass flows are divided transversely to the main direction of flow by mixing elements attached to the rotor element as a consequence of the movement of the rotor element and the filler compound is mostly urged away against the main direction of flow. Consequently, the filler compound can flow in behind the mixing element and a rearrangement and layer formation of the components of the filler compound can be achieved in this manner. More difficult mixing tasks result in longer mixers, a larger force expenditure and thus increased energy consumption for the mixer drive unit and in greater resistance to urge the components through the mixer.

The following disadvantageous consequences therefore had to be coped with up to the present moment: a longer mixer, an increased energy consumption and also an increased pressure loss. Accordingly, larger and heavier drive units and batteries for the discharge device have to be provided, which restricts the handling for the application of the mixture, increases the energy requirement and reduces the duration of operation of the discharge device in the case of battery operation.

Since the components react with one another and harden in the mixer on an interruption of the discharge, the mixer must be replaced and disposed of after use and together with the components contained therein.

It is therefore the object of the invention to find a mixer for difficult mixing tasks which is short and manages with as little energy effort for the rotor element as possible as well as with a smaller pressure loss as compared to the prior art mixer. The mixers are produced in high volumes. Small mixers provide savings with respect to the material for the mixer, the components and also costs for the disposal of the used mixers.

The object of the invention is satisfied by a dynamic mixer for a plurality of fluid components which contains a housing and a rotor element which is rotatably arranged in the housing. The housing has an inlet opening for at least one respective component and at least one outlet opening, with a ring-shaped intermediate space being provided between the rotor element and the housing in which a mixing element connected to the rotor element is arranged. The housing includes a first antechamber, a second antechamber and a main chamber, with the second antechamber being arranged downstream of the first antechamber so that the first antechamber can be traversed by the components before the components enter the second antechamber.

According to an embodiment, the components are guided radially from the housing in the direction of the rotor element in the second antechamber and are premixed by mixing elements attached at the housing side or at the rotor element before they are led into the main chamber after a deflection in the axial direction. A mixing element is preferably provided in the second antechamber. A mixing element can be provided in the first antechamber.

In accordance with an embodiment, the mixing element can be formed as a pin element. In accordance with a further embodiment, the mixing element can be formed as a carrier element or as an arm element. The carrier element or arm element can in particular have a curvature, with the curvature of the front side in particular being convex and/or the curvature of the rear side being concave.

In accordance with a further embodiment, the mixing element in the main chamber can have at least one vane element which can be formed as a directing element for conveying the components from the inlet opening to the outlet opening. The at least one vane element can in particular not cover more than 50% of a plane which is placed through the intermediate space, which contains the vane element and which is aligned normal to the rotor axis.

A first vane element and a second vane element can be arranged downstream of the first vane element, with the shortest spacing between the first vane element and the second vane element amounting to at least one third of the spacing between the rotor element and the main chamber defined by the boundary of the second housing part.

In accordance with a further embodiment, an outlet opening for the passage of the components is provided between the second antechamber and the main chamber and the housing. In accordance with a further embodiment, a rotary surface is arranged between the second antechamber and the first antechamber.

The rotor element can in particular be supported in the first housing part in accordance with each of the preceding embodiments. An apparatus for piercing a container containing the components can be provided at at least one of the inlet openings of the first housing part.

The mixing ratio of the first and second components can be 1:1, but can also lie at 1:10 to 1:50 or even higher.

The use of the dynamic mixer preferably takes place for viscous or thick two-component systems such as seals, bond connections, impression materials disposed in autonomous hand discharge units or in stationary desktop units.

If the components are distributed evenly in space, albeit not mixed, in a first premixing step in accordance with the invention, it is possible to achieve a good mixing by a local mixing action involving much less energy expenditure compared to previously known solutions. It could also be shown that the dwell time of the components in the dynamic mixer can be reduced for a required mixing effect and the dynamic mixer can thus be constructed more compactly overall and with less volume content.

The invention will be explained in the following with reference to the drawings. There are shown.

Figure 1A:
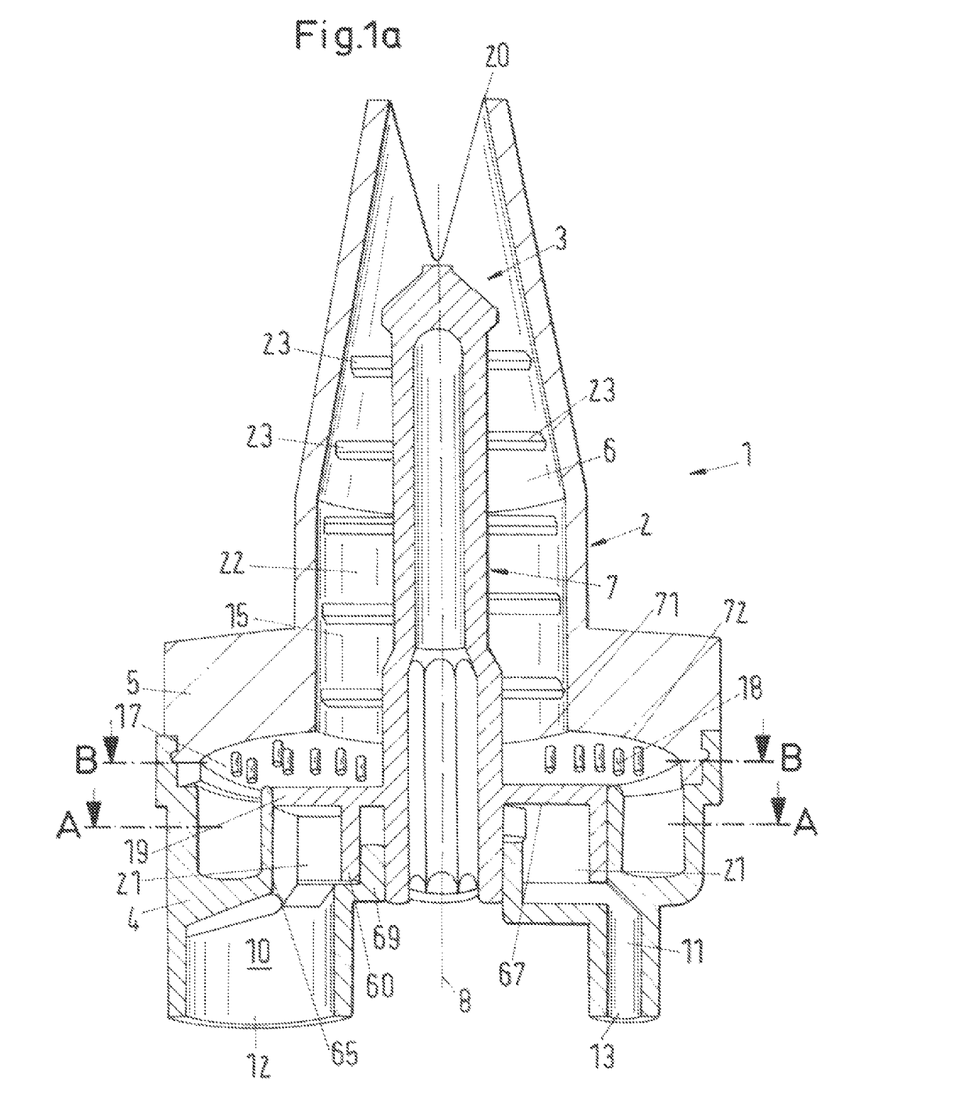
FIG. 1a a section through a dynamic mixer in accordance with a first embodiment of the invention along the rotor axis.

FIG. 1a shows a dynamic mixer for a plurality of fluid components. The dynamic mixer 1 has a housing 2 and a rotor element 3 which is arranged rotatably about a rotor axis 8 in the housing 2. In the present embodiment, the housing 2 is made in two parts; it contains a first housing part 4 in which the inflow of the components is located and a second housing part 5 which serves for the production of a mixture from the plurality of fluid components. The first housing part 4 is connected to the second housing part 5 via a latch connection, a snap-in connection or a weld connection as soon as the rotor element 3 is received in the second housing part 5. The first housing part 4 has an inlet opening 12, 13 for at least one respective component. The inlet openings 12, 13 can have different diameters which are dependent on the desired mixing ratio of the components. The inlet openings open into corresponding inlet passages 10, 11 which are arranged in the first housing part 4. The inlet passages 10, 11 open into the first antechamber 21 which is provided with outlet openings which are not shown in FIG. 1 and which open into an inner space 15 of the second housing part 5.

The second housing part 5 has at least one outlet opening 20. The mixture of the components exits the dynamic mixer through the outlet opening 20. The outlet opening 20 can be especially designed in accordance with the intended use. In the present case, a V-shaped incision is provided. The form of a triangular bead results on the discharge of the filler compound with the help of this V-shaped incision. The inner space 15 of the second housing part 5 serves for the reception of the rotor element 3. The inner space 15 is bounded by the inner wall 6 of the second housing part 5. The inner space 15 is formed, at least at the points at which the rotor element 3 is located, as a ring-shaped intermediate space.

The inner space 15 has a second antechamber 17 and a main chamber 22. The components are directed from the second antechamber 17 to the main chamber 22. A premixing can already take place in the second antechamber 17. A plurality of mixing elements 18 are arranged in the second antechamber for this purpose. These mixing elements are designed, for example, as shown here, as pin elements which project into the second antechamber 17. The pin elements can be arranged on a rotary surface 19 of the rotor element 3 and/or can project from the inner wall of the housing bounding the antechamber into the antechamber 17. Shear forces are exerted onto the components by the rotary surface 19 and the pin elements 18.

Alternatively, a fixed disk element which can have pin elements as needs be can be arranged above the rotary surface 19. At least one outlet opening for the passage of the components into the second antechamber can be arranged in the disk element. The disk element can be clamped between the first and second housing parts.

A ring-shaped intermediate space in which a mixing element 7 connected to the rotor element 3 is arranged is provided between the rotor element 3 and the inner wall 6 of the housing.

The mixing element 7 includes a plurality of vane elements 23 in the main chamber 22. The vane elements 23 protrude as projections into the inner space 15 which forms the main chamber 22. The complete mixing of the components takes place in this main chamber 22 in that the components are taken up by the vane elements and are rearranged. At least some of the vane elements can be formed as a directing element for conveying the components through the inner space 15 in the direction of the outlet opening 20.

The rotor element is formed at least partly as a hollow body. The central hollow space of the rotor element serves for receiving a drive shaft. The hollow space advantageously has an at least triangular shape so that a drive shaft can be rotationally fixedly connected to the rotor element so that the rotor element can be driven via the drive shaft.

The dynamic mixer accordingly contains at least two antechambers. The first antechamber 21 is used for introducing the components, with a coarse premixing being able to be achieved in the first antechamber. The second antechamber 17 serves for achieving a local mixing. The first antechamber 21 is designed such that two or more components are introduced into the first antechamber 21 such that the component having the smaller volume flow is introduced into the volume flow of the component having the larger volume flow. The first antechamber 21 is separated from the second antechamber 11 by a rotary surface 19, in particular a cover plate, which can be arranged at the rotor element 3. In the first antechamber 21, the one component is guided away from the inlet passage 11 to the outlet opening of the inlet passage 10 of the other component by means of a vane element attached to the rotor element and/or to the housing or a separate stator, whereby at least one first distribution of the components and/or a first premixing of the components to a filler compound takes place. The premixed components move from the first antechamber 21 into the second antechamber 17 via an outer ring gap, which is formed by the mixer housing and the cover plate. In the second antechamber 17, the premixed components move radially to the rotor axis 8 and are mixed further locally with little force expenditure over small obstacles such as pin elements. The filler compound is directed from the second antechamber 17 into the main chamber 22. After an axial deflection in the transition region between the first antechamber 17 and the main chamber 22, the filling compound moves to the centrally disposed outlet opening 20. A complete mixing takes place in the main chamber 22 using further vane elements or static mixing elements.

Figure 1B:
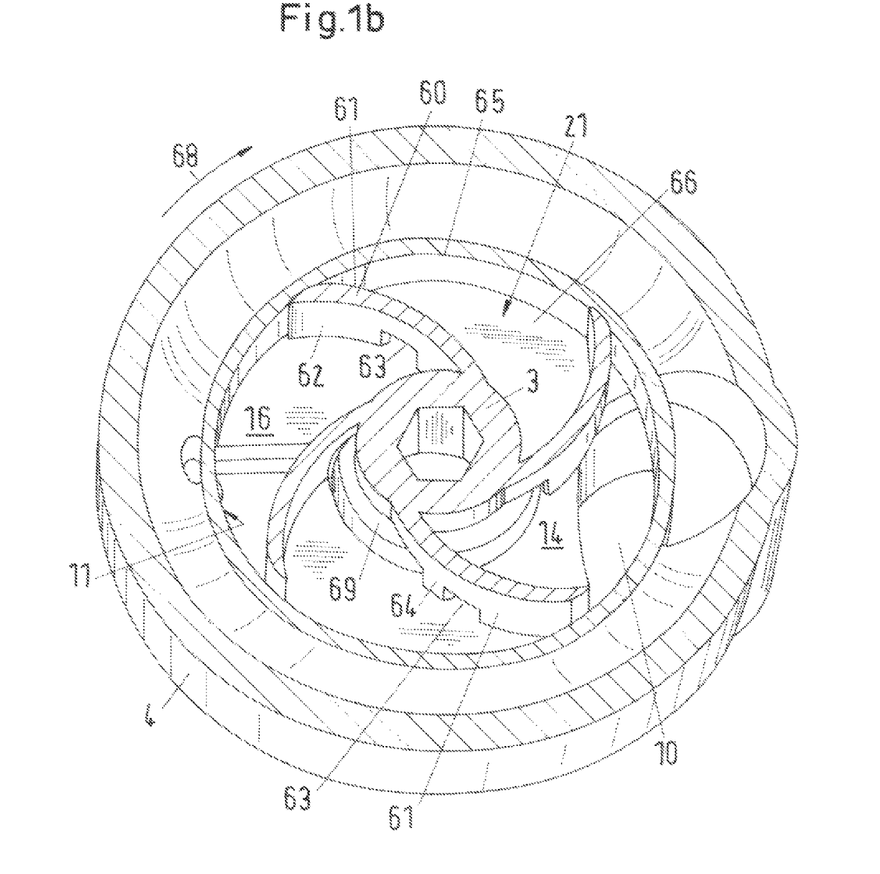
FIG. 1b a section through the dynamic mixer in accordance with FIG. 1 through the first antechamber.

The first antechamber 21 is visible in FIG. 1b in a section through the dynamic mixer in the region of the first housing part 4. The position of the section is given by A-A in FIG. 1a. The section plane is laid normal to the rotor axis and extends through the first antechamber. The two inlet passages 10, 11 open into the first antechamber 21. An arm element 60 which is connected to the rotor element 3 is located in the first antechamber. A plurality of such arm elements 60 can naturally be provided; in FIG. 1b, four arm elements of the same type are shown.

The arm element 60 extends through the first antechamber 21 from the rotor element 3 up to the inner wall 65 of the first housing part 4 which bounds the first antechamber. The arm element 60 has a front side 61 by means of which the filler compound is displaced through the first antechamber 21 and has an oppositely disposed rear side 62. The rear side 62 has a concave curvature; the front side 61 has a convex curvature. The curvature radii of the curvatures of the rear side and of the front side are advantageously substantially the same. The arm element 60 extends from the base 68 up to the top 67 of the prechamber 21. The top 67 is only visible at the rotary surface 19 in FIG. 1a. A cut-out 63 can be provided in the arm element 60 when a part of the filler compound should escape from the front side 61 to the rear side 62.

Furthermore, the arm element 60 has a guide cut-out 64. The arm element slides by means of the guide cut-out 64 on a projection 69 of the first housing part. The rotor element is also held by the projection in the dynamic mixer.

Figure 1C:
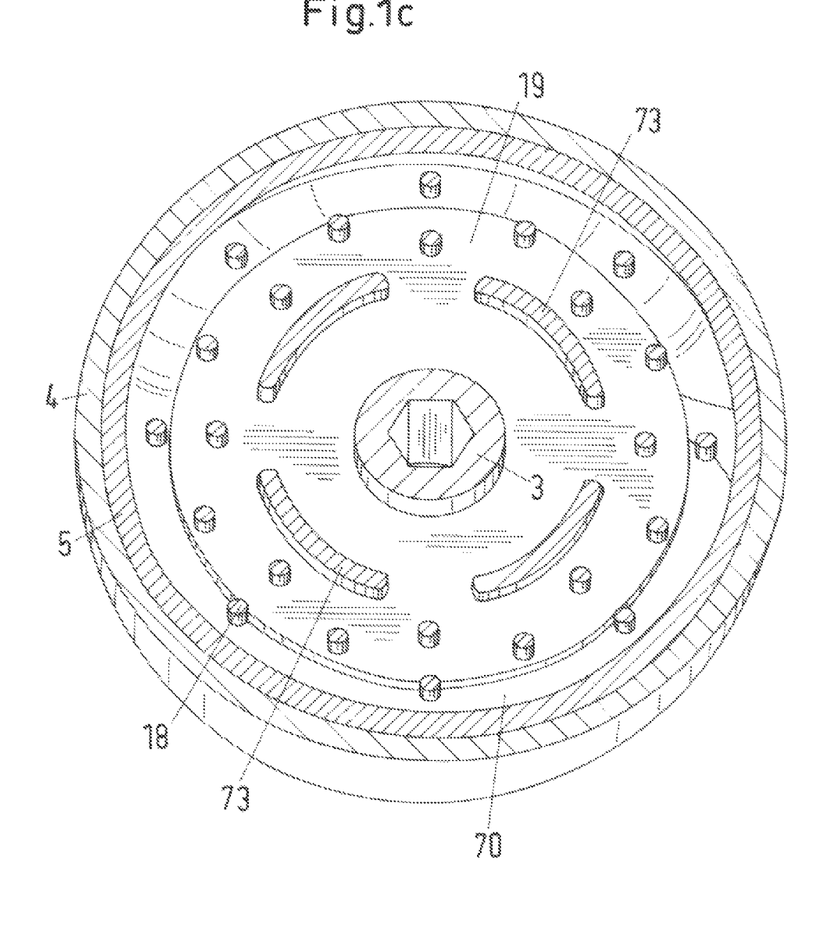
FIG. 1c a section through the dynamic mixer in accordance with FIG. 1 through the second antechamber.

FIG. 1c shows a section through the second antechamber 17. This section through the dynamic mixer is laid between the first housing part 4 and the second housing part 5 in the region of the connection. The position of the section is given by B-B in FIG. 1a. The section plane is laid normal to the rotor axis 8. The rotary surface 19 forms the base of the second antechamber 17. The filler compound enters into the second antechamber through a ring gap 70 and exits the second antechamber via a ring-shaped outlet opening 71 which is only visible in FIG. 1a. A plurality of pin elements 18 are located in the second antechamber. The pin elements 18 project from the top 72 into the second antechamber 17. The filler compound is urged at least partly into a rotary movement by shear forces which are introduced by the rotary surface 19. When the filler compound reaches one of the pin elements, it divides into two part flows, whereby a rearrangement and a premixing of the components of the filler compound take place with a minimal force expenditure. Wall element sections 73 can additionally be provided. The wall element sections 73 are arranged substantially around the outlet opening 71 (see FIG. 1a) and enforce a uniform throughflow of the second antechamber before the entry into the main chamber. The wall element sections 73 project from the top 72 into the second antechamber 17. The wall element sections 73 are designed as cylinder segments. The inner diameter of the cylinder segments substantially corresponds to the inner diameter of the outlet opening 71 or respectively corresponds to the inner diameter of the main chamber 22 formed by the second housing part 65 at its inlet.

Figure 2A:
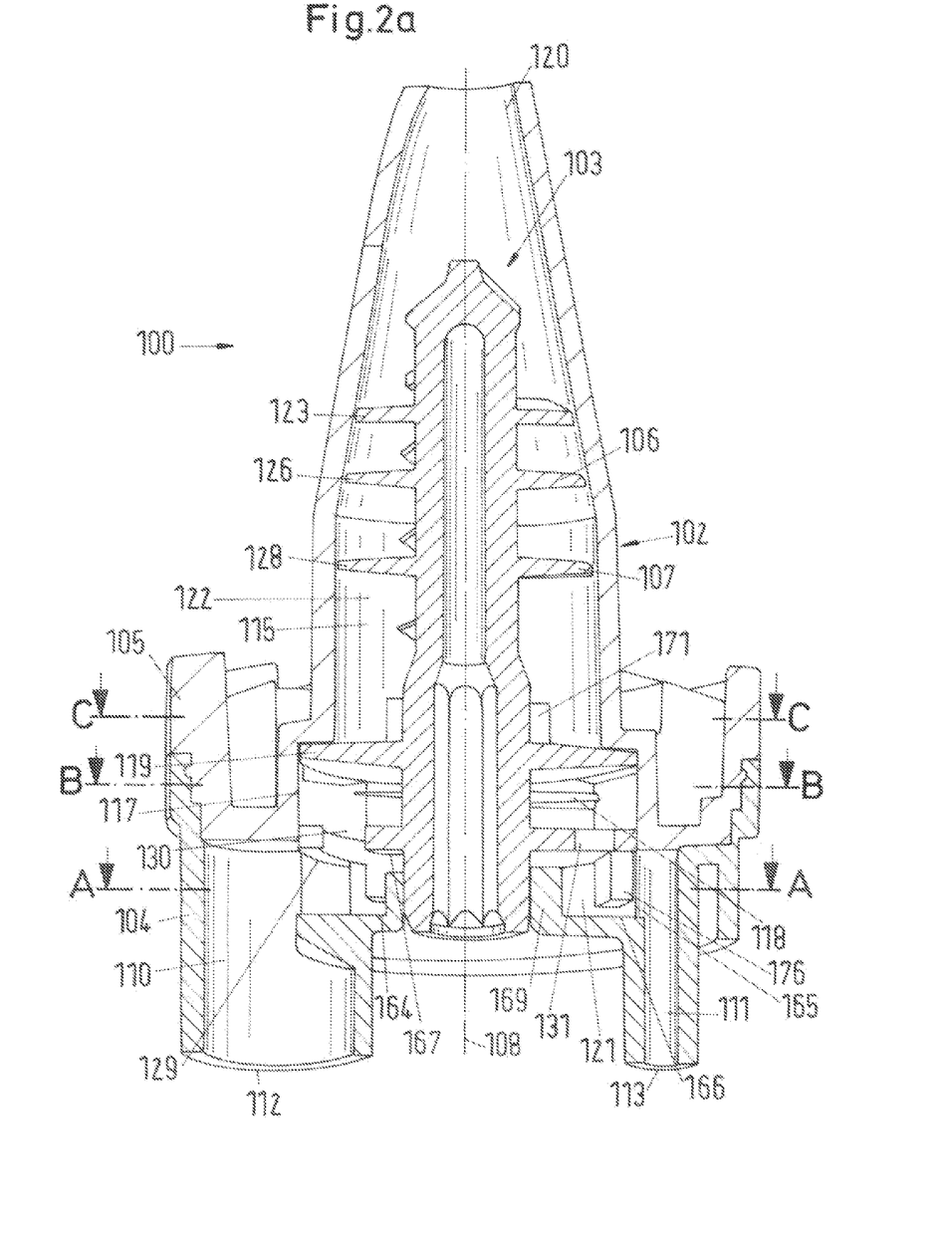
FIG. 2a a section through a dynamic mixer in accordance with a second embodiment of the invention.

FIG. 2a shows a section through a dynamic mixer in accordance with a second embodiment of the invention for the mixing of a plurality of fluid components. The dynamic mixer 100 has a housing 102 and a rotor element 103 which is arranged rotatably about a rotor axis 108 in the housing 102. In the present embodiment, the housing 102 is made in two parts; it contains a first housing part 104 in which the inflow of the components is located and a second housing part 105 which serves for the production of a mixture from the plurality of fluid components. The first housing part is connected to the second housing part via a latch connection, a snap-in connection or a weld connection as soon as the rotor element 103 is received in the second housing 105. The first housing part 104 has a respective inlet opening 112, 113 for at least one respective component. The inlet openings 112, 113 can have different diameters which are dependent on the desired mixing ratio of the components. The inlet openings open into corresponding inlet passages 110, 111 which are arranged in the first housing part 104. The inlet passages 110, 111 open into the first antechamber 121 which is provided with outlet openings 130, 131 which open into the second antechamber 117 of the second housing part 105.

The second housing part 105 has at least one outlet opening 120. The mixture of the components exits the dynamic mixer through the outlet opening 120. The main chamber of the second housing part 105 serves for the reception of the rotor element 103.

The components are directed from the second antechamber 117 to the main chamber 122. A further mixing can take place in the second antechamber 117. A mixing element 118 is arranged in the second antechamber for this purpose. The mixing element 118 is formed as a vane element which is connected to the rotor element 103. A ring-shaped intermediate space in which a mixing element 107 connected to the rotor element 103 is arranged is provided in the main chamber 122 between the rotor element 103 and the inner wall of the housing.

The mixing element 107 includes a plurality of vane elements 123 in the main chamber 122. The vane elements 123 protrude as projections into the inner space 115 which forms the main chamber 122. The complete mixing of the components takes place in this main chamber 122 in that the components are taken up by the vane elements and are rearranged. At least some of the vane elements are formed as a directing element for conveying the components through the inner space 115 in the direction of the outlet opening 120.

It is also not necessary that adjacent vane elements arranged behind one another with respect to the rotor axis 108 have the same spacing from one another. The spacing of the vane element 123 arranged closest to the outlet opening 120 from the vane element 126 is, for example, smaller than the spacing of the vane element 126 from the vane element 128.

Figure 2B:
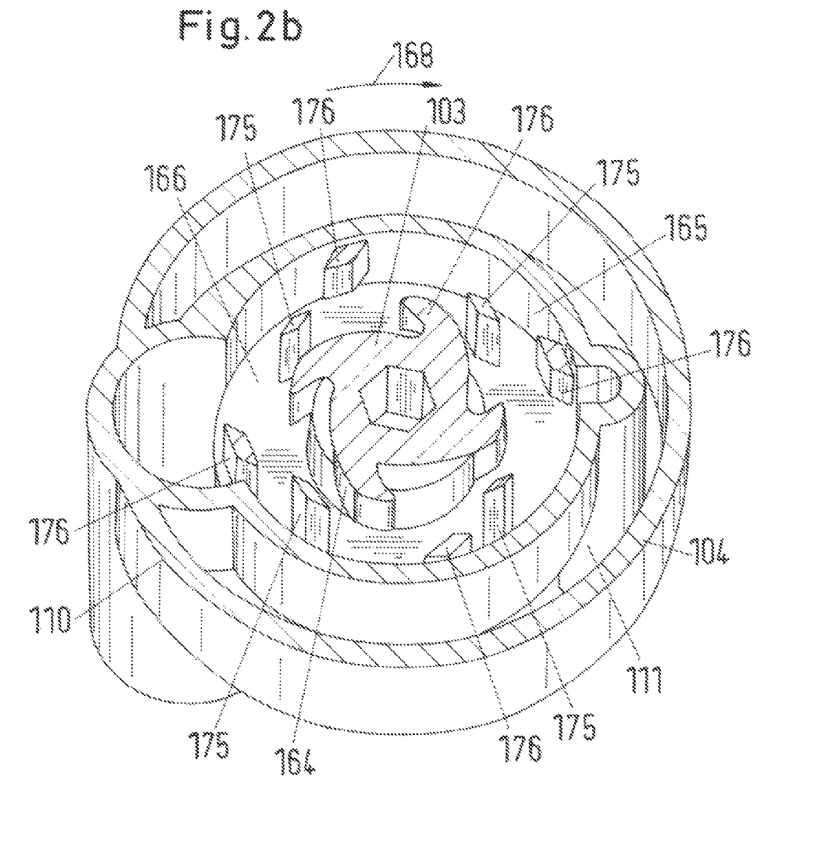
FIG. 2b a section through the dynamic mixer in accordance with FIG. 2a through the first antechamber.

The first antechamber 121 is visible in FIG. 2b in a section through the dynamic mixer in the region of the first housing part 104. The position of the section is given by A-A in FIG. 2a. The section plane is laid normal to the rotor axis and extends through the first antechamber 121. The two inlet passages 110, 111 open into the first antechamber 121. In the first antechamber 121, disturbance elements 175 are arranged which project from the base 166 of the antechamber 121 into the antechamber. These disturbance elements are stationary and divide the filler compound flow. In the direction of rotation 168, they advantageously have an initially continuously increasing cross-section which passes through a maximum and then continuously decreases. The cross-section can in particular be formed in diamond shape. The carrier elements 176 are designed in a similar manner to the disturbance elements 175. They project from the rotary surface 129 into the first antechamber 121. These carrier elements 176 are moved along with the rotary surface 129 when the rotor element 103 carries out a rotary movement. The outer carrier elements 176 scrape off the components from the outlet openings of the passages 110, 111 and lead them into the first prechamber 121. An unchanging mixing ratio of the components is achieved by these measures. The carrier elements 176 and the disturbance elements 175 together effect a distribution of the components and a first premixing thereof in the filler compound before they move via outlet openings 130 and 131 into the second antechamber 117. The outlet openings 130, 131 are arranged in the rotary surface 129 and are shown in FIG. 2a.

The top 167 of the first antechamber is only visible at the rotary surface 129 in FIG. 2a. The inner wall 165 which is a part of the first housing part 104 extends between the base 166 and the top 167.

The inner carrier elements 176 can form a guide cut-out 164 together with the hub of the rotor element 103 and the rotary surface 129. The rotor element 103 slides by means of the guide cut-out 164 on a projection 169 of the first housing part. The rotor element 103 is also held by the projection 169 in the dynamic mixer.

Figure 2C:
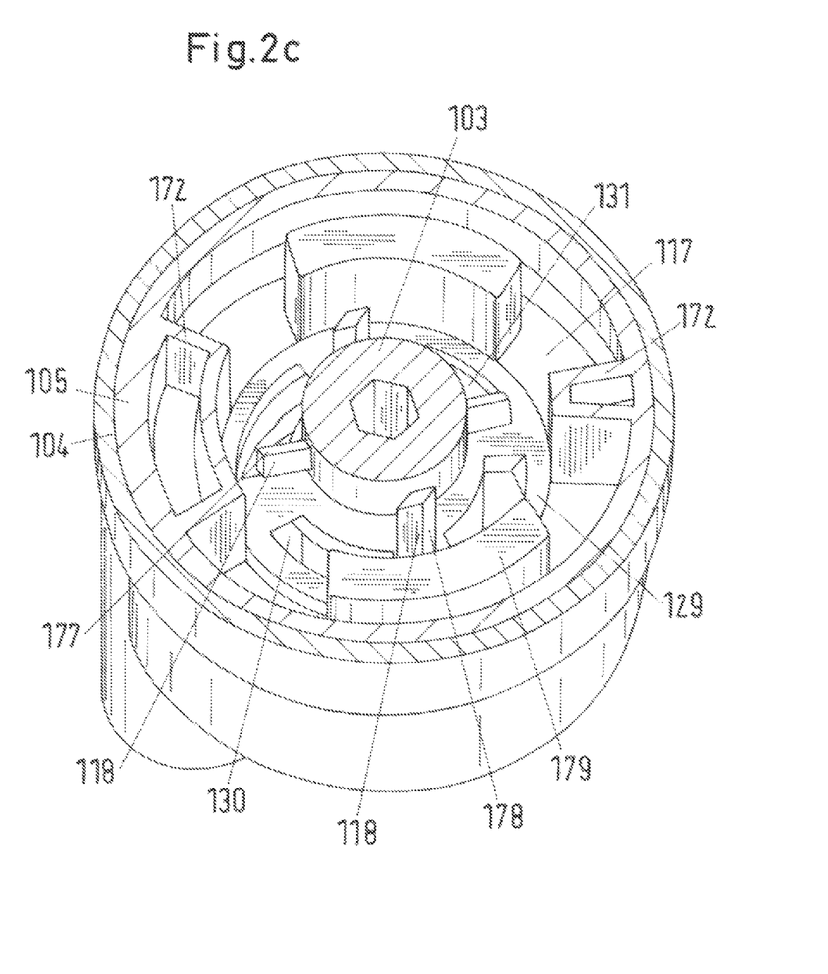
FIG. 2c a section through the dynamic mixer in accordance with FIG. 2a through the second antechamber.

FIG. 2c shows a section through the second antechamber 117. This section through the dynamic mixer is laid in the region of the connection between the first housing part 104 and the second housing part 105. The position of the section is given by B-B in FIG. 2a. The section plane is laid normal to the rotor axis 108. The rotary surface 119 forms the top of the second antechamber 117. The rotary surface 129 forms the base of the second antechamber 117.

Figure 2D:
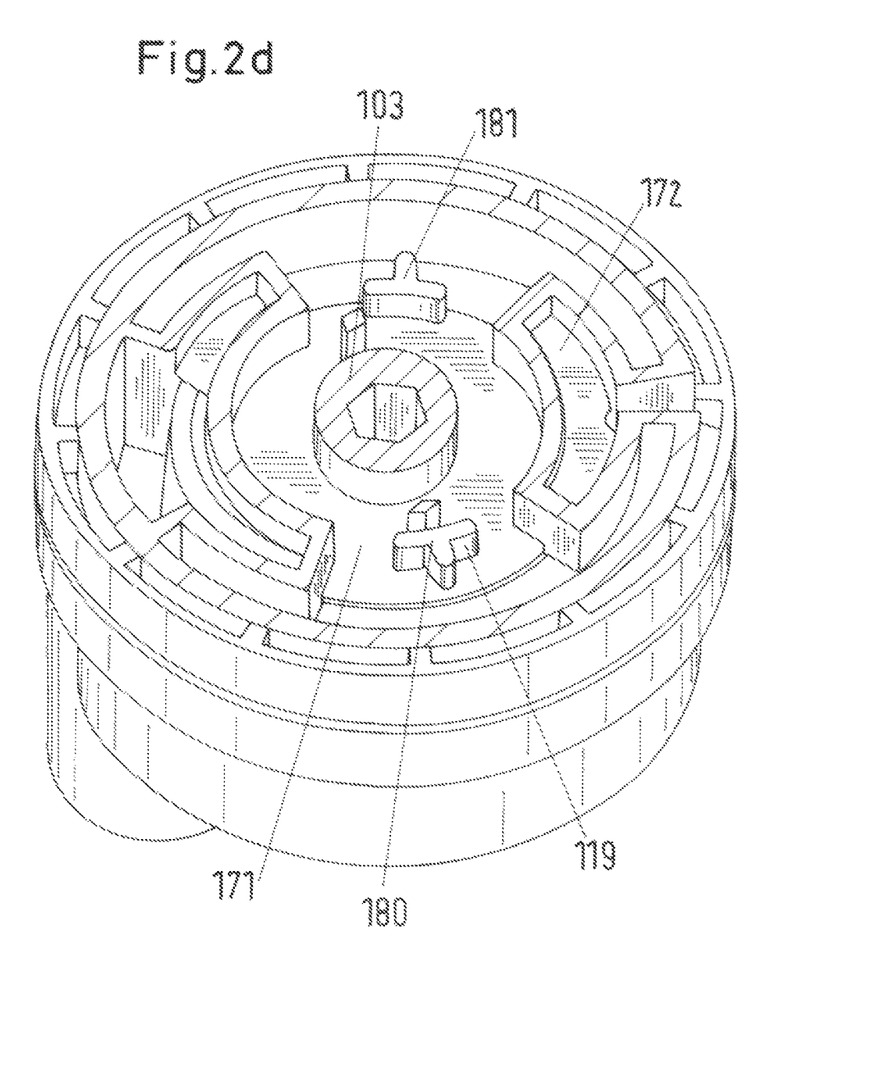
FIG. 2d a section through the dynamic mixer in accordance with FIG. 2a through the main chamber.

The filler compound enters in accordance with FIG. 2c through the outlet openings 130, 131 of the first antechamber 121 into the second antechamber 117 and exits the second antechamber 117 via at least one outlet opening 171 which is visible in FIG. 2d. A plurality of mixing elements 118 are located in the second antechamber 117. The mixing elements 118 project from the rotor element 103 or from the rotary surface 129 or from the rotary surface 119 into the second antechamber 117. The filling compound is urged at least partly into a rotary movement by shear forces which are introduced by the rotary surface 119 and by the rotary surface 129.

The mixing elements 118 can be designed as vane elements 177, 178, with the geometrical dimensions applying to the carrier element 176 being able to apply to the vane element 178. The components, are mixed both in a plane parallel to and in a plane perpendicular to the axis of rotation by the vane elements 178 at the rotary surface 119 together with the vane elements 177.

Additional cylinder segment blocks 179 are formed as part of the first housing part 104. Boundaries 172 are provided which are formed as part of the second housing part 105 to design the passage region from the second antechamber 117 into the main chamber 122 as a restriction. The filler compound has to be guided via this restriction so that it can only enter into the main chamber 122 after passing through the restriction, that is it is channeled in a restricting manner from the second antechamber 117 to the main chamber 122.

The entry region of the main chamber 122 is visible in FIG. 2d in a section through the dynamic mixer in the region of the second housing part 105. The position of the section is given by C-C in FIG. 2a. The side of the rotary surface 119 facing the main chamber 119 is partly covered by a top element 172 of the second housing part 105. The filler compound enters into the main chamber 122 through the outlet opening 171.

Additional guide elements 180 can be provided in or directly adjoining the outlet opening 171 to better distribute the inflow of the components into the main chamber 122.

The components inflowing in the axial direction and forming a pasty filler compound are redirected in the middle, that is transversely to the rotor axis 108, into a mixing chamber which was called a first antechamber in the above. The component flowing into the first antechamber 121 having the smaller volume flow is integrated as much as possible into the volume flow of the component having the larger volume flow, by vane elements or carrier elements 176 arranged at the rotor element 103 from the outlet openings of the inlet passages 110, 111 and is directed into the first antechamber 121 where the filler compound is subjected to a first coarse mixing by the carrier elements 176 and/or the disturbance elements 175. The first antechamber 121 is bounded in the direction of the outlet opening 120 by a disk element which is located at the rotor element 103 and which forms a rotary surface 129. This disk element has at least one opening and/or forms a ring gap with the housing at the periphery. The opening and/or the ring gap allow a throughflow of the filler compound into a second antechamber 117. The components can be further admixed here by radial and/or axial vane elements 177, 178. The openings foreseen in the second antechamber 117 subsequently direct the filler compound into the mixing region of the main chamber 22, 122 into which they can flow radially. The axial, arcuate vane elements 138 especially applied as needs be in the inflow region of the main chamber 122 shear off the filler compound directly on the entry into the main chamber 122 and convey the filler compound in the direction of the rotor axis 108. At least some of the vane elements 123, 126, 128, 137 have radial directing elements conveying in the direction of the outlet opening 120. Beside the dynamic mixer components of the rotor element and any present fixed directing and/or disturbance elements, the dynamic mixer can also additionally have static mixer components in the main chamber 122.

It has been shown that the mixing task in the main chamber 22, 122 is substantially reduced by the introduction of the second antechamber 17, 117 in which an additional premixing takes place by a local distribution of the components with a relatively small flow resistance and a small torque of the rotor element 3, 103. Therefore the construction length of the dynamic mixer in accordance with each of the embodiments can be shortened overall substantially, the content can be reduced and the mixing energy to be applied can be decreased.

Figure 3:
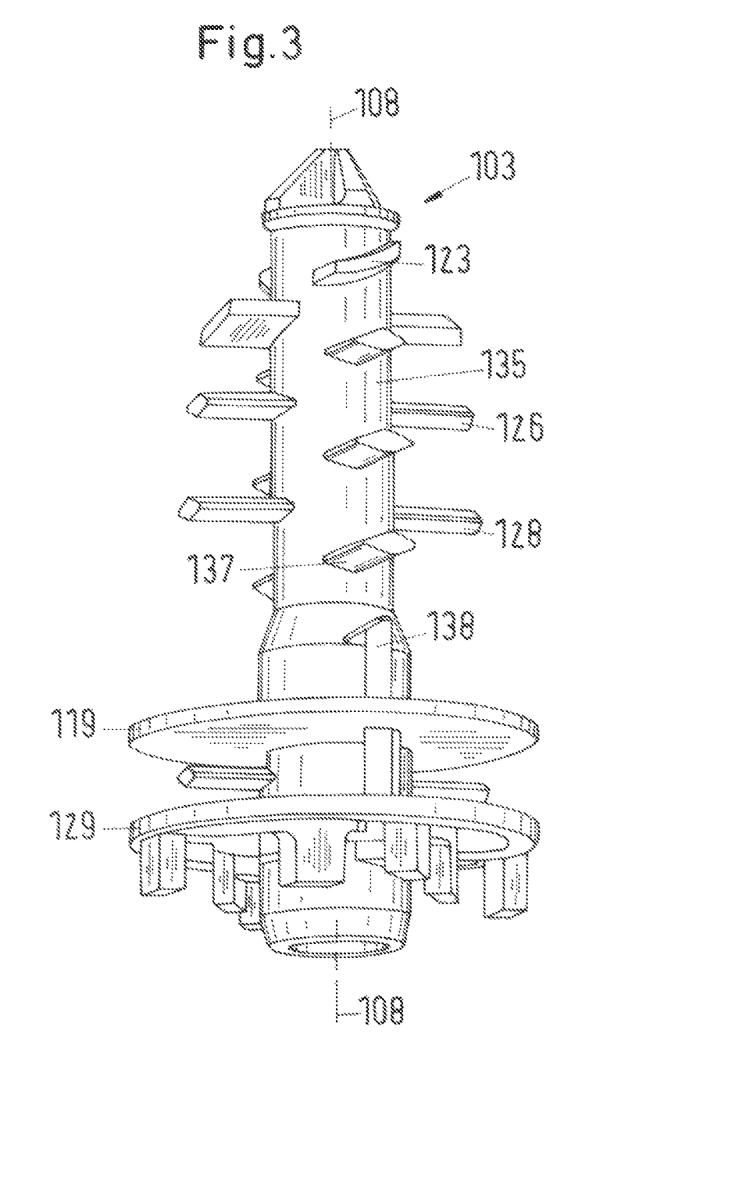
FIG. 3 a view of a rotor element for a dynamic mixer.

FIG. 3 shows a view of a rotor element for use in one of the dynamic mixers in accordance with one of the preceding embodiments. The rotor element corresponds to the rotor element 103 shown in FIG. 2a so that the same reference numerals as in FIG. 2a are used for the same parts. However, this reference is not to be understood as a restriction such that the rotor element can only be used in connection with the embodiment in accordance with FIG. 2a. It is rather the case that the rotor element can likewise be used in a housing in accordance with any one of the other embodiments with a slight adaptation of the geometry of the housing. The rotor element 103 has a rotor axis 108 along which a rotor element hub 135 is arranged. The rotor element hub 135 carries a rotary surface 129 which contains the outlet openings 130, 131. The components which are supplied from the inlet passages 110, 111 (see FIG. 2a) to the first antechamber exit into the second antechamber 117 through these outlet openings 130, 131. A second bounding of the second antechamber 117 is formed by the rotary surface 119 which is attached downstream of the rotary surface 129 on the rotor element hub 135. At the peripheral side, the second antechamber 117 is bounded by the second housing part 105 (see FIG. 2a).

The components are premixed in a plane parallel to the rotor element hub 135 by a mixing element 118, which is arranged in the second antechamber 117 on the rotor element hub 135, in a plane perpendicular to the rotor element hub and by any further mixing elements, which project from the rotary surface into the second antechamber 117. To move into the main chamber 122 (see FIG. 2a), the components flow around the rotary surface 119. A narrow ring-shaped gap through which the components pass remains between the rotary surface 119 and the inner wall of the second housing part. Furthermore, vane elements 123, 126, 128 which can be designed as directing elements and in this case exert a conveying effect on the filler compound in the direction of the outlet opening 20, 120, are arranged downstream of the rotary surface 119 in the main chamber 22, 122. In addition, vane elements 137 can be provided which are formed in diamond shape as described, for example, in WO98/43727. Furthermore, an arcuate vane element 138 is shown which is directly adjacent the rotary surface 119 and shears off the filler compound from the inlet openings and directs it into the main chamber 22, 122. Similar vane elements can also be arranged further downstream and effect a scraping of the filler compound from the wall of the main chamber 22, 122.

Vane elements of the same type are preferably arranged opposite one another at the same height, with the height being measured along the rotor axis 108.

Alternatively, the rotor element can extend only up to the input region into the main chamber 22, 122, in accordance with any of the preceding embodiments. A static mixing element can be arranged in the main chamber itself, which is not shown in the drawing.

The invention claimed is:

1. A dynamic mixer for a plurality of fluid components, comprising:
a housing having
at least one inlet opening for receiving a mixable component into the dynamic mixer and opening to a corresponding at least one inlet passage,
at least one outlet opening,
a first antechamber into which the corresponding at least one inlet passage opens, the first antechamber having a base that is a first longitudinal end of the first antechamber and a top that is a second longitudinal end of the first antechamber,
a second antechamber arranged downstream of the first antechamber, the first antechamber being arranged so as to be traversed by the mixable components before the second antechamber, and the first antechamber and the second antechamber being separated by a rotary surface, and
a main chamber,
the first and second antechambers and the main chamber being configured to enable the mixing of the mixable components;
a rotor element rotatably arranged in the housing, the rotor element and the housing being separated by a ring-shaped intermediate space;
a first mixing element connected to the rotor element arranged in the intermediate space; and
a second mixing element arranged in the first antechamber so as to be disposed on a cartridge side of the rotary surface, the second mixing element including curved extensions that are each configured as a carrier element or as an arm element, each curved extension extending from the rotor element substantially to an inner wall of the first antechamber and having a convex front side facing toward a direction of movement of the second mixing element in a circumferential direction about the rotor axis, and a concave rear side facing in a direction away from the direction of movement of the second mixing element in the circumferential direction about the rotor axis, each curved extension further extending longitudinally from the base to the top of the first antechamber.

2. The dynamic mixer in accordance with claim 1, further comprising
a third mixing element configured to guide and premix the mixable components in the second antechamber, the third mixing element guiding the mixable components in a radial direction from the housing toward the rotor element,
the third mixing element being attached to the housing or to the rotor element to deflect the mixable components in an axial direction before the mixable components are guided into the main chamber.

3. The dynamic mixer in accordance with claim 2, wherein
the third mixing element is a pin element.

4. The dynamic mixer in accordance with claim 1, wherein
the first mixing element has at least one vane element arranged in the main chamber, the vane element being configured to direct the mixable components from the inlet opening to the outlet opening.

5. The dynamic mixer in accordance with claim 4, wherein
the at least one vane element covers a maximum of 50% of a plane disposed through the intermediate space, the plane containing the vane element and being aligned normal to the rotor axis.

6. The dynamic mixer in accordance with claim 1, wherein
the outlet opening for the passage of the components is disposed radially between the second antechamber and the main chamber and the housing.

7. The dynamic mixer in accordance with claim 1, wherein the rotor element is supported in a first housing part, the first housing part having the inlet openings.

8. The dynamic mixer in accordance with claim 1, wherein
the rotary surface is a cover plate arranged at the rotor element to direct the mixable components from the first antechamber to the second antechamber.

9. The dynamic mixer in accordance with claim 1, wherein
the first antechamber is configured for a coarse premixing of the mixable components such that a component having a smaller volume flow can be mixed with a component having a larger volume flow.

10. The dynamic mixer in accordance with claim 1, wherein
the at least one outlet opening includes at least two outlet openings disposed upstream of the second antechamber and a central outlet opening disposed downstream of the second antechamber.

11. The dynamic mixer in accordance with claim 1, wherein
the at least one inlet opening includes a first inlet opening configured to receive a first volume flow of mixable component and a second inlet opening configured to receive a second volume flow of mixable component, the second volume flow being larger than the first volume flow.

12. The dynamic mixer in accordance with claim 1, wherein
one of the arm element and the carrier element are arranged as projections that extend radially from the rotor element to the inner wall of the housing.

13. The dynamic mixer in accordance with claim 3, wherein
the pin element includes projections extending from a top surface of the second antechamber and is configured to divide a flow of mixable components.

14. A dynamic mixer for a plurality of fluid components, comprising:
a housing having
at least one inlet opening for receiving a mixable component into the dynamic mixer and opening to at least one corresponding inlet passage,
a first antechamber receiving at least one inlet passage, the first antechamber having a base that is a first longitudinal end of the first antechamber and a top that is a second longitudinal end of the first antechamber,
a second antechamber arranged downstream of the first antechamber,
a main chamber arranged downstream of the second antechamber,
at least one outlet opening disposed downstream of the main chamber; and
a rotor element rotatably arranged in the housing and having a rotary surface arranged between the second antechamber and the first antechamber,
the first antechamber having a plurality of arm elements disposed therein, each of the plurality of arm elements being disposed on a cartridge side of the rotary surface and extending between the rotor element and an inner wall of the housing and longitudinally from the base to the top of the first antechamber,
the second antechamber having a plurality of axial projections disposed therein and extending from one of the rotary surface of the rotor element and the inner wall of the housing, at least two of the axial projections being arranged at different radial distances from the rotor element.

15. A dynamic mixer for a plurality of fluid components, comprising:
a housing having
at least one inlet opening for receiving a mixable component into the dynamic mixer and opening to at least one corresponding inlet passage,
a first antechamber receiving at least one inlet passage, the first antechamber having a base that is a first longitudinal end of the first antechamber and a top that is a second longitudinal end of the first antechamber,
a second antechamber arranged downstream of the first antechamber,
a main chamber arranged downstream of the second antechamber,
at least one outlet opening disposed downstream of the main chamber; and
a rotor element rotatably arranged in the housing and having a rotary surface arranged between the second antechamber and the first antechamber,
the first antechamber having a plurality of carrier elements and disturbance elements disposed therein, the carrier elements extending radially from a center axis of the rotor element substantially to an inner wall of the first antechamber and being disposed on a cartridge side of the rotary surface of the first antechamber, the carrier elements being configured to rotate with the rotary surface when the mixer is in use, the disturbance elements being projections extending axially from a stationary base of the first antechamber such that the disturbance elements are stationary with respect to the carrier elements when the mixer is in use,
the second antechamber having a plurality of mixing elements disposed therein, each projecting radially from one of the rotor element and the rotary surface.

* * * * *